United States Patent [19]

Jenkins et al.

[11] Patent Number: 4,667,506
[45] Date of Patent: May 26, 1987

[54] HIGH PRESSURE CONTAINER TESTER

[75] Inventors: John B. Jenkins, Thornhill; John D. Scott; Alois Simon, both of Willowdale, all of Canada

[73] Assignee: Crown Cork & Seal Canada Inc., Ontario, Canada

[21] Appl. No.: 803,174

[22] Filed: Dec. 2, 1985

[51] Int. Cl.[4] ............................................. G01M 3/22
[52] U.S. Cl. ........................................ 73/45.2; 73/49.2
[58] Field of Search ................ 73/45.2, 45.1, 45, 37, 73/49.2

[56] References Cited

U.S. PATENT DOCUMENTS

| | | | |
|---|---|---|---|
| 2,985,008 | 5/1961 | Renard | 73/45.2 |
| 3,178,932 | 4/1965 | Stuchbery et al. | 73/45.2 |
| 3,307,390 | 3/1967 | Behrens et al. | 73/45.2 |
| 3,874,226 | 4/1975 | Weber | 73/45.2 |

FOREIGN PATENT DOCUMENTS 42177 4/1977 Japan ..................................... 73/45.2

Primary Examiner—Stewart J. Levy
Assistant Examiner—Joseph W. Roskos
Attorney, Agent, or Firm—Arne I. Fors; Robert F. Delbridge

[57] ABSTRACT

A method and apparatus for pressure testing containers in peripheral cells in a rotating turret is disclosed in which high pressure air in tested containers is initially discharged into a low pressure reservoir down to a predetermined low pressure and the residual air at the low pressure then discharged to the atmosphere with little sound generation. Incoming containers to the testing apparatus are initially supplied with pressurized air at a low pressure from the low pressure air reservoir and then supplied with pressurized air from a high pressure air supply, preferably a high pressure air reservoir, to achieve the desired test pressure. The low pressure reservoir and the high pressure reservoir are incorporated in the rotating turret structure and are in communication with a closure cap for each cell by distribution means including a double-acting valve during selected portions of rotation of the turret.

8 Claims, 8 Drawing Figures

HIGH PRESSURE CONTAINER TESTER

BACKGROUND OF THE INVENTION

The present invention relates to a method and apparatus for testing containers and, more particularly, relates to a method and apparatus for individually testing containers for structural strength and for flaws which might cause ruptures or leaks when the containers are sealed with pressurized contents.

In-line machine testing of containers such as bottles or cans to pressures up to about 230 pounds per square inch gauge (psig) to test structural flaws in the container is well known. Containers are fed sequentially to a testing machine and high pressure air introduced into the containers for a predetermined period of time after which the air is exhausted to the atmosphere. This procedure is not only energy inefficient because of the high volumes of pressurized air required but also creates a hazardous work environment because of the loud ear-damaging sounds emitted by the escaping air.

U.S. Pat. No. 3,751,973 issued Aug. 14, 1973 discloses a bottle testing method and apparatus for pressure testing bottles and for possible flaws in which bottles are fed through an opening in a stationary shield to a rotating turret having peripheral cells. Each cell is sealed while pressurized air is forced into the bottles and, prior to exhausting air from tested bottles, coupling means are provided to communicate the tested bottles directly with bottles entering the testing sequence to reduce compressed air requirements. This apparatus requires a fairly complex conduit system for interconnecting discharging bottles with incoming bottles.

SUMMARY OF THE INVENTION

The present invention is directed to a method and apparatus for pressure testing containers in a rotating turret in which high pressure air in tested containers is initially discharged into a low pressure reservoir down to a predetermined low pressure and the residual air at the low pressure then discharged to the atmosphere with little sound generation. Incoming containers to the testing apparatus are initially supplied with pressurized air at a low pressure from the low pressure air reservoir and then supplied with pressurized air from a high pressure source such as a compressor fed chamber or reservoir to acheive the desired test pressure.

In its broad aspect, the apparatus of the present invention for pressure testing containers comprises the combination of a turret rotatable about a support shaft having a plurality of test cells parallel to the axis of the turret about the periphery thereof, each cell having an open end facing in the same direction; means for rotating the turret; means for sequentially feeding containers with their open ends facing outwardly to said cells as the turret rotates; means for closing said cells after admission of containers, said closure means having sealing means for concurrently abutting and sealing the open end of each cell and its container and isolating the interior of the container from the cell, and having means for introducing air under pressure into the container; means for actuating said closure means; a high pressure air supply; a low pressure air reservoir; distribution means communicating the high pressure air supply and the low pressure air reservoir with the closure means pressurized air introducing means; and valving means operatively connected to said distribution means for initially introducing air under pressure from the low pressure reservoir and subsequently from the high pressure supply to the containers and, upon completion of testing, discharging air under pressure from the containers to the low pressure reservoir down to a predetermined low pressure and exhausting residual air at said predetermined low pressure to the atmosphere during selected portions of rotation of the turret prior to discharge of the containers from the cells.

In a preferred embodiment of the invention, the high pressure air supply includes a high pressure chamber, said high pressure chamber and the low pressure air reservoir being incorporated into the turret structure for rotation therewith. The closure means comprise a circular cap having an annular pad and a central pad of resilient compressible material incorporated therein for abutting the open end of the cell and the rim of the container for isolating the interior of the container from the cell and for sealing the cell and container from the atmosphere.

The method of the invention, in its broad aspect, comprises sequentially feeding containers to be tested to test cells arranged about the periphery of a rotating turret, closing each said test cell with a container therein and isolating the interior of the container from the cell, introducing air under a low pressure from a low pressure reservoir into the container and then introducing air under a high pressure from a high pressure source into the container to achieve a desired test pressure, exhausting the air under pressure upon completion of testing into the low pressure reservoir down to a predetermined low pressure, exhausting residual air to the atmosphere, and discharging the tested containers from the rotating turret. The method of the invention preferably includes forming an annulus in each test cell about a container for receiving air which may leak from a container due to a flaw in the container and providing a pressure switch responsive to the pressure of air in the annulus whereby an increase of annulus air pressure actuates said pressure switch to stop the introduction of pressurized air to the container.

BRIEF DESCRIPTION OF THE DRAWING

The invention will now be described with reference to the accompanying drawings, in which.

DESCRIPTION OF THE PREFERRED EMBODIMENT OF THE INVENTION

Figure 1:
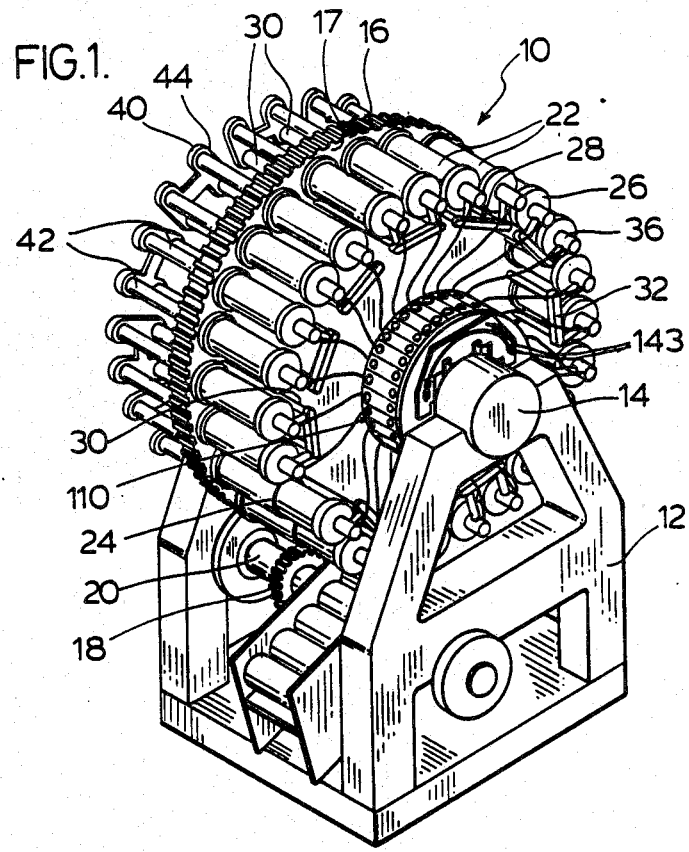
FIG. 1 is a perspective view of the pressure testing apparatus of the invention.

With reference to FIG. 1, the high pressure tester of the invention comprises turret 10 mounted for rotation on base 12 about shaft 14 extending therethrough. Ring gear 16 formed about the periphery of carrier wheel 17 is meshed with and driven by pinion gear 18 mounted on drive shaft 20 which in turn is driven by an electric motor, not shown.

Figure 3:
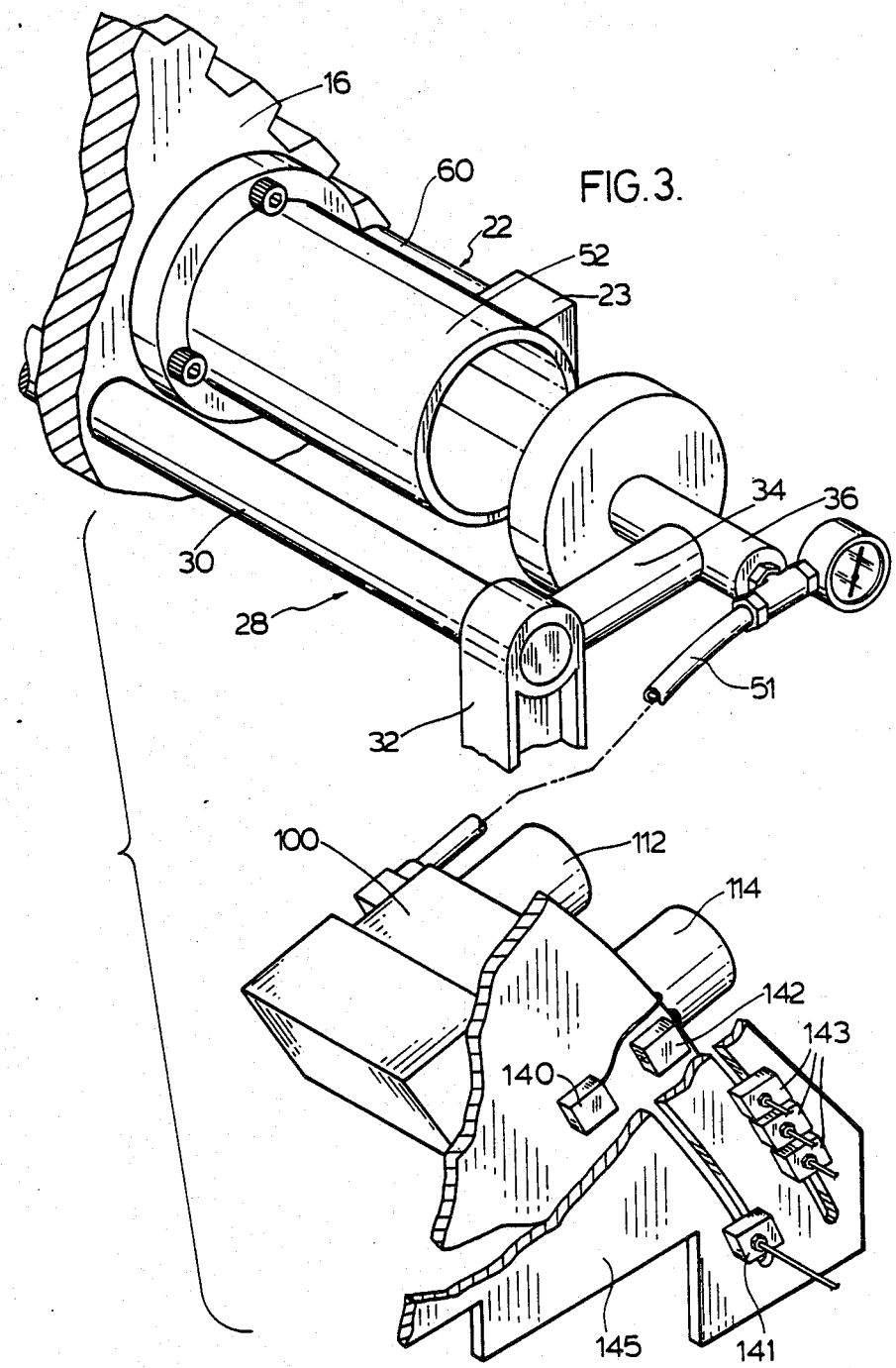
FIG. 3 is a perspective view of a test cell of the invention in a partially open position, magnet and switch controls for regulating pressurized air to the test cells, and control valve with solenoids.

Rotatable turret 10 has a plurality of test cells 22 mounted in proximity to its periphery on carrier wheel 17 with open end 24 of each cell facing in the same direction, i.e. to the right as viewed in FIG. 1. Each of test cells 22 has a closure member 26 reciprocally mounted for axial movement away from and towards the open end 24 of each cell 22 by means of a reciprocating support 28 shown most clearly in FIGS. 3 and 5. Each support 28 comprises a pair of parallel, spaced-apart shafts 30, one of which is shown, slidably mounted for reciprocal axial movement through carrier wheel 17, each pair of shafts having at their forward ends a transverse member 32 with a pair of depending members 34 rigidly secured thereto. Members 34 are secured at their opposite distal ends to cylindrical stems 36 of a pair of adjacent test cells.

The opposite ends of shafts 30, projecting rearwardly through carrier wheel 17, are connected to cross-head member 40 which in turn is secured to the rear ends of a pair of shafts 42 which extend forwardly through carrier wheel 17 into a pair of adjacent test cells. Each test cell 22 comprises a cylindrical side wall 52 having a flanged base 53 mounted on the wall 54 of carrier wheel 17 such as by bolts 57. The closed or rear end 44 of each cell 22 has ejector disk 46 mounted therein for reciprocal travel on a shaft 42. A rubber ring 56 seated in annular groove 59 formed in the rear side of disk 46 is adapted to seat in and compress in central cavity 61 formed in base 53 to seal shaft 42 and to function as a shock absorber when cell 22 closes.

Figure 5:
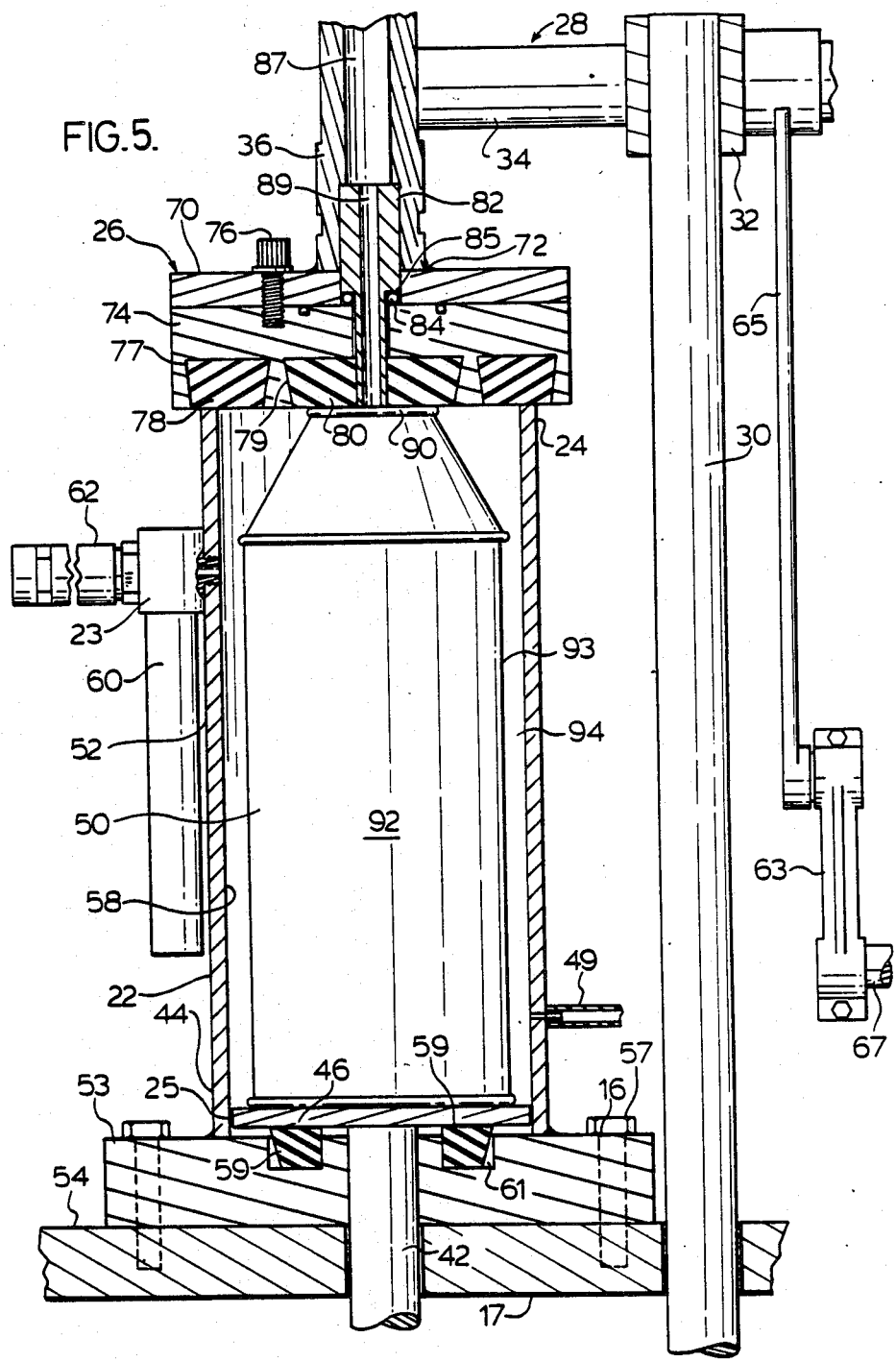
FIG. 5 is a longitudinal sectional view of a test cell with closure device abutting the cell rim and container rim.

With reference to FIG. 5, a crank 63 is connected to transverse member 32 by rod 65 to extend and retract a pair of shafts 30 upon rotation of shaft 67. In operation, the concurrent opening of a pair of adjacent cells 22 is effected by extending shafts 30 to axially separate closure members 26 from the open ends 24 of the test cells with concurrent extension of shafts 42 into the test cells for ejection of containers 50 contained therein.

Each test cell 22 has a pressure switch such as an ASCO ® pressure switch 60 threaded into a mounting block 23 which in turn is threaded into the side of the cell wall 52 for communication with the interior of cell 22. Pressure switch 60 is set at a pressure of about 5 psig such that an increase of air pressure in test cell 22 over 5 psig will actuate the pressure switch for reasons which will become apparent as the description proceeds. A pressure valve 62 set to open at a pressure of about 10 psig is also threaded into mounting block 61.

Closure member 26 mounted on stem 36 comprises circular cap 70 welded at 72 to stem 36. Clamping pad 74 formed of a metal such as aluminum is removably secured to cap 70 by, for example, three screws 76 threaded thereinto, one of which is shown. Clamping pad 74 has an outer annular cavity 77 containing annular pad 78 and an inner central cavity 79 with pad 80 of a resilient compressible material such as high density rubber mounted therein. A replaceable metal insert 82 is seated within the end of stem 36 and is locked therein by means of abutment of clamping pad 74 against 0-ring 84 which in turn is seated against insert annular shoulder 85 of insert 82.

Stem 36 and insert 82 have co-axial openings 87, 89 for communicating pressurized air to the interior of container 50 in test cell 22. The abutment of container rim 90 for compression against resilient inner pad 80 provides an effective seal between the interior 92 of container 50 and the annulus 94 formed between the side wall 93 of container 50 and the inner surface 58 of wall 52 of test cell 22. Annulus 94 is sealed from the atmosphere by means of resilient outer pad 78 which abuts the rim 24 of test cell 22.

Figure 8:
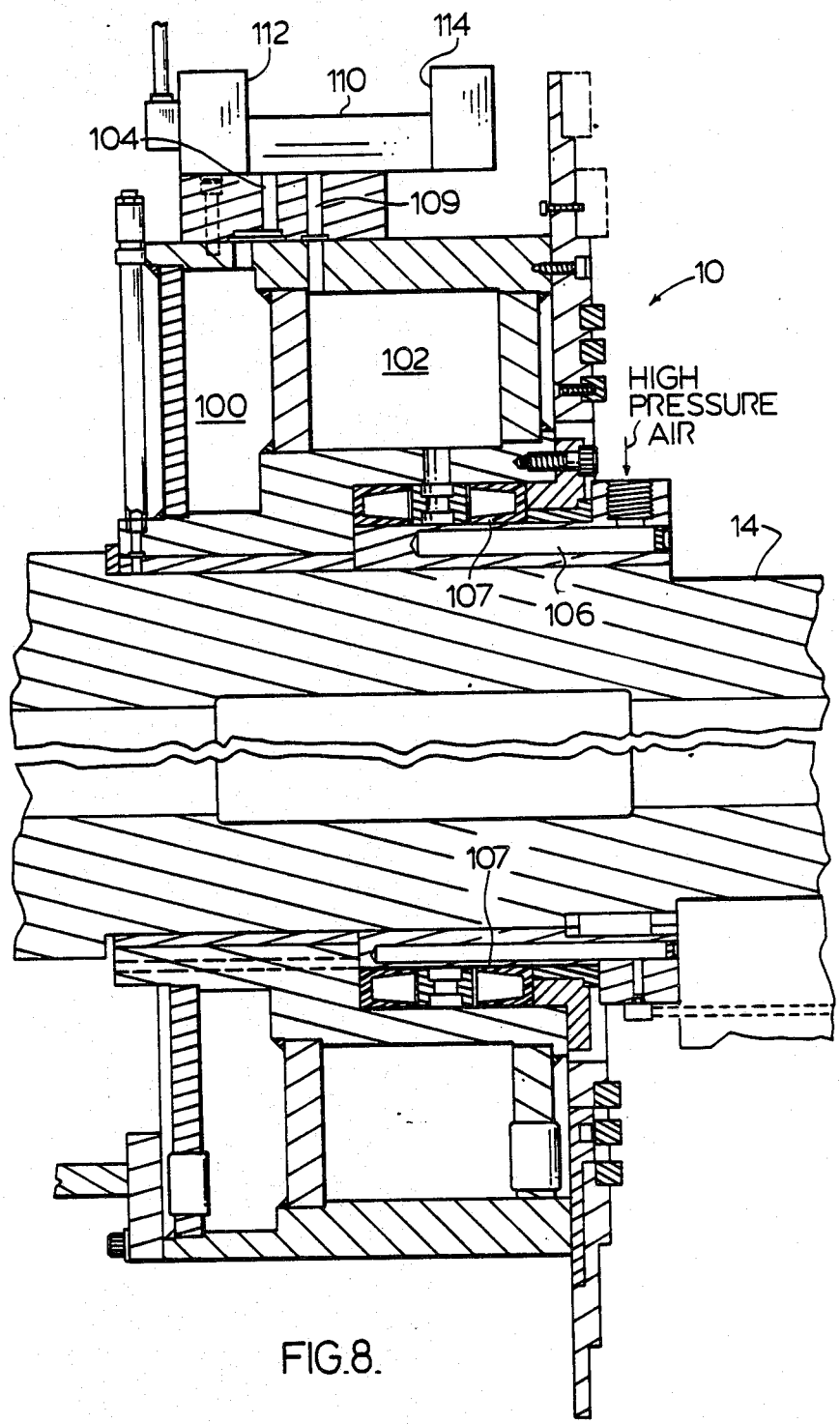
FIG. 8 is a sectional view of the central portion of the turret showing the relationship of low and high pressure air reservoirs.

Referring now to FIG. 8, turret 10 has incorporated therein a pair of annular pressure chambers or reservoirs 100 and 102. Chamber 100 is a low pressure reservoir having a plurality of equispaced radial passageways 104, one of which is shown, for ingress and egress of low pressure air from and to valves 110. Chamber 100 is maintained as a pressure of up to, for example, about 25 psig. Chamber 102 is a high pressure chamber fed with pressurized air at a pressure of about 150 psig from a compressor, not shown, by way of passageway 106 adjacent stationary shaft 14. An air seal is maintained between shaft 14 and turret 10 by a fluorocarbon ring seal 107. Radial passageways 109 provide high pressure air to valves 110.

Figure 6:
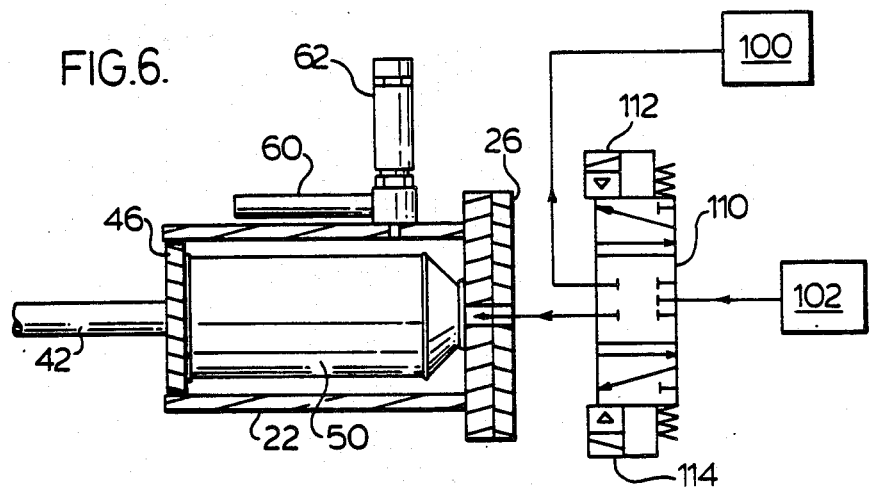
FIG. 6 is a schematic view showing the relationship of test cell illustrated in FIG. 5 with control valve.
Figure 7:
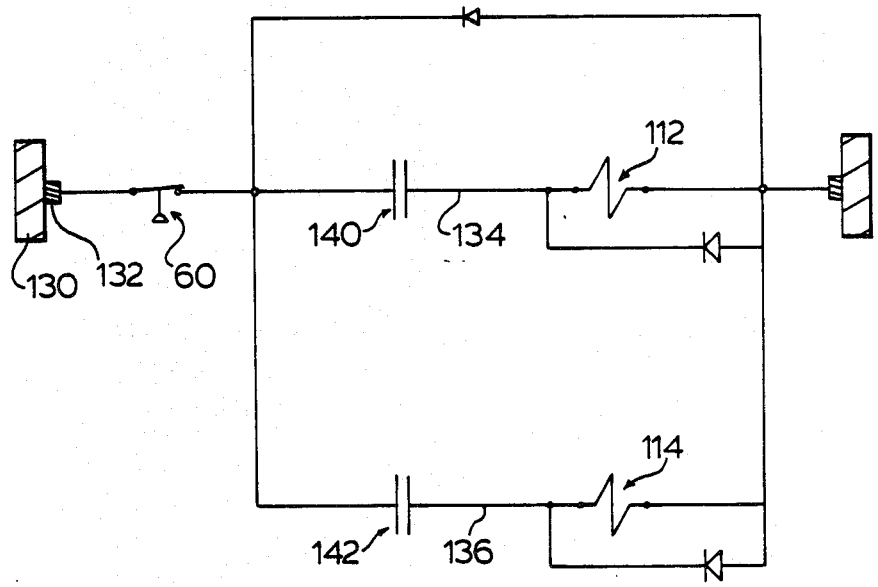
FIG. 7 is a schematic view of the electrical circuit for actuating the control valve.

Turning now also to FIGS. 6 and 7, each double-acting reciprocating air valve 110 has a low pressure solenoid 112 at one end and a high pressure solenoid 114 at the other end. A plurality of valves 110 is mounted equispaced about turret 10 at one end thereof, one valve 110 for each test cell 22, for control of air flow between chambers 100, 102 and its respective test cell 22.

Figure 4:
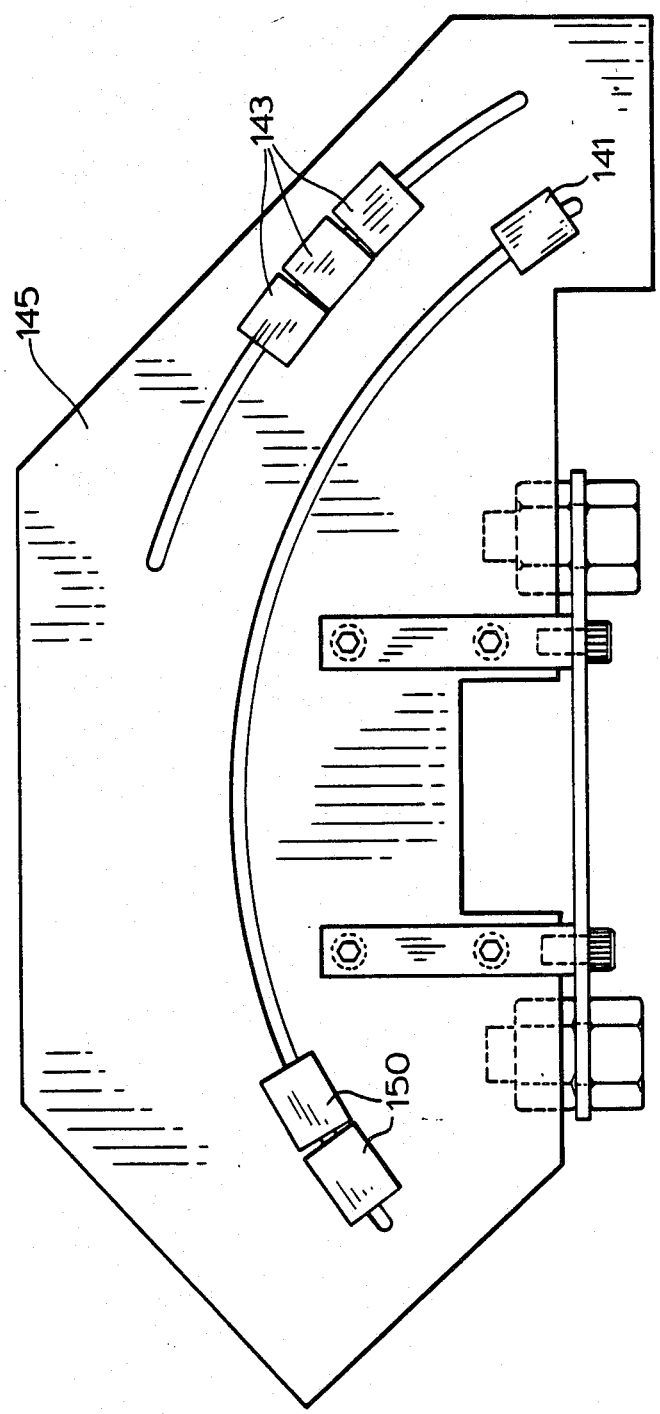
FIG. 4 is a plan view of magnetic controls.

With particular reference now to FIG. 7, it will be seen that a low volta9e power supply provided by means of stationary slip ring 130 is in continuous electrical communication with rotating brush 132 on turret 10 for the supply of power through pressure switch 60 on each cell 22 to parallel circuits 134, 136 which communicate with low pressure solenoid 112 and high pressure solenoid 114, respectively, of valve 110. A reed switch 140 mounted on turret 10 is actuated by stationary magnet 141 on plate 145 shown in FIGS. 1, 3 and 4 as the turret rotates to energize solenoid 112 which opens valve 110 to the low pressure reservoir and initially introduces low pressure air at a pressure of about 25 psig into container 50 through line 51. Reed switch 142 is then actuated by magnets 143 to reverse switch 110 and communicate high pressure chamber 102 to the interior of container 50 for the introduction of high pressure air at a pressure of about 150 psig into the container 50 through line 51.

Figure 2:
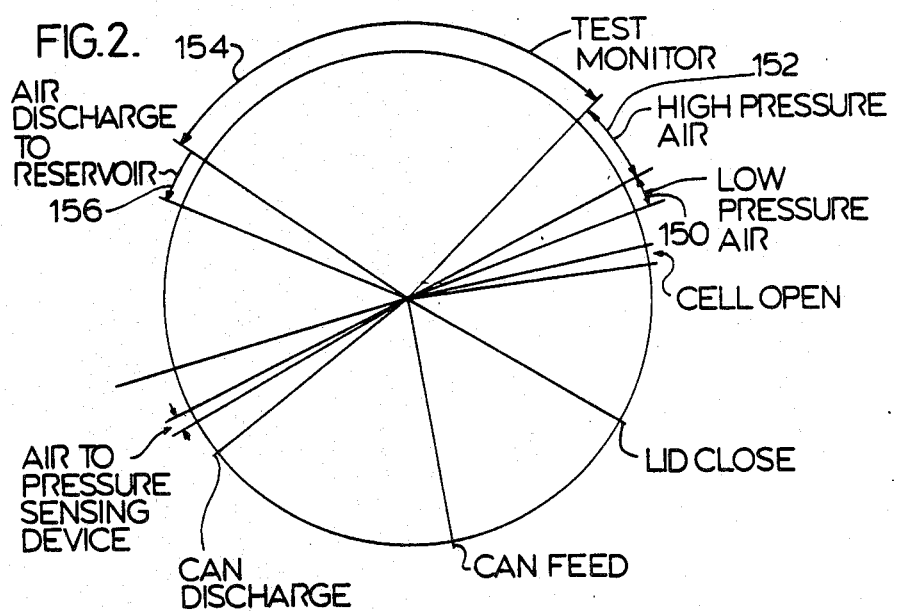
FIG. 2 is a graphical illustration of the sequence of pressure testing steps in a testing cycle.

Turning now to FIG. 2, it will be seen that low pressure air is initially introduced during an angle of turret rotation depicted by the arc 150 followed by high pressure air introduction during rotation through an angle of rotation depicted by arc 152 to increase the pressure in container 50 to a test pressure of about 150 psig. This pressure is maintained during rotation through the angle depicted by arc 154 at the completion of which solonoid 112 is again energized by magnets 151 to reverse valve 110 and communicate container 50 with the low pressure chamber 110 thereby allowing the high pressure air to escape from the tested container to the low pressure chamber down to a pressure of about 25 psig during angular rotation through arc 156. Closure member 26 is then opened allowing the relatively quiet escape of residual air at low pressure followed by the ejection of container 50 by actuation of ejector disk 46.

Prior to the admission of low pressure air depicted by arc 150 at the start of the test cycle, the cell is temporarily opened to purge air compressed during the introduction of container 50.

In the event the container should be faulty due to a flaw in the container rim or rupture of the container wall or a container seam, allowing air pressure to escape into annulus 94, normally-closed pressure switch 60 will detect the pressure increase when the pressure reaches 5 psig and will open to de-energize solenoids 112, 114 and close valve 110 to prevent additional supply of air to the test cell receiving air. A pressure signal is also emitted through line 49 and a rotating valve during rotation through arc 155 in FIG. 2 to actuate an ejector device, not shown, which will eject the faulty container contained in the test cell to a waste bin.

The present invention provides a number of important advantages. High pressure air from tested containers is returned to a low pressure central reservoir allowing rapid depressurization of the container with subsequent exhaust of the residual air at a predetermined low pressure to the atmosphere, thereby conserving pressurized air and precluding the generation of loud and high pitched sounds which are injurious to personnel.

It will be understood, of course, that modifications can be made in the embodiment of the invention illustrated and described herein without departing from the scope and purview of the invention as defined by the appended claims.

What we claim as new and desire to protect by Letters Patent of the United States is:

1. An apparatus for pressure testing containers comprising, in combination, a turret rotatable about a support shaft having a plurality of test cells parallel to the axis of the turret about the periphery thereof, each cell having an open end facing in the same direction; means for rotating the turret; means for sequentially feeding containers with their open ends facing outwardly to said cells as the turret rotates; means for closing said cells after admission of containers, said closure means having sealing means for concurrently abutting and sealing the open end of each cell and its container and isolating the interior of the container from the cell, and having means for introducing air under pressure into the container; means for actuating said closure means; a high pressure air supply; a low pressure air reservoir; distribution means communicating the high pressure air supply and the low pressure air reservoir with the closure means pressurized air introducing means; and valving means operatively connected to said distribution means for initially introducing air under pressure from the low pressure reservoir and subsequently from the high pressure supply to the containers and, upon completion of testing, discharging air under pressure from the containers to the low pressure reservoir down to a predetermined low pressure and subsequently exhausting residual air at low pressure to the atmosphere during selected portions of rotation of the turret prior to discharge of the containers from the cells.

2. An apparatus for pressure testing containers as claimed in claim 1 in which the high pressure air supply includes a high pressure chamber, said high pressure chamber and said low pressure reservoir being incorporated into the turret for rotation therewith.

3. An apparatus for pressure testing containers as claimed in claim 2 in which said closure means comprise a hollow stem, a circular cap rigidly secured on one side to said stem coaxial therewith, a rigid clamping pad co-extensive with said cap secured on the other side thereto, said clamping pad having on the opposite side an outer annular cavity and a central cavity, an annular pad and a central pad of resilient compressible material mounted in said annular cavity and said central cavity for abutting in sealing engagement the open ends of a cell and a container respectively.

4. An apparatus for pressure testing containers as claimed in claim 3 in which said means for introducing air under pressure into the containers comprise the hollow stem rigidly secured to the cap co-axial therewith, said cap having a central opening in communication with the hollow stem, and a hollow insert mounted in said stem for communicating air under pressure to the containers.

5. An apparatus for pressure testing containers as claimed in claim 3 in which said high pressure supply and said low pressure reservoir are incorporated into the turret structure for rotation therewith and said valving means mounted on the turret independently communicating each cell with the high pressure supply and low pressure reservoir.

6. An apparatus for pressure testing containers as claimed in claim 5 in which each test cell has a pressure switch in communication therewith and an electrical circuit for communicating a signal from the pressure switch to the valving means for closing the valving means to the introduction of air to the containers upon actuation of the pressure switch by an increase of pressure in the test cell.

7. An apparatus for pressure testing containers as claimed in claim 6 in which said means for actuating the closure means comprises a pair of parallel, spaced-apart shafts mounted for reciprocal axial travel in the turret adjacent a pair of test cells, means for interconnecting said shafts at both ends, means for connecting said shafts at one end to a pair of closure stems for extending and retracting the clamping pads secured thereto towards and away from the cell open ends, and crank means for reciprocating said pair of shafts during selected portions of rotation of the turret for admitting and ejecting containers from the cells.

8. A method for pressure testing containers comprising sequentially feeding containers to be tested to test cells arranged about the periphery of a rotating turret, closing each said test cell with a container therein and isolating the interior of the container from the cell, introducing air under a low pressure from a low pressure reservoir into the container and then introducing air under a high pressure from a high pressure source into the container to achieve a desired test pressure, forming an annulus in each test cell about a container for receiving air which may lead from the container due to a flaw in the container and providing a pressure switch responsive to an increase of pressure of air in the annulus whereby an increase of annulus air pressure actuates said pressure switch to stop the introduction of pressurized air to the container, exhausting the air under pressure upon completion of testing into the low pressure reservoir down to a predetermined low pressure, exhausting residual air to the atmoshphere, and discharging the tested containers from the rotating turrent.

* * * * *